United States Patent

Hart et al.

[11] Patent Number: 5,690,655
[45] Date of Patent: Nov. 25, 1997

[54] SUTURE TENSIONING DEVICE

[75] Inventors: Rickey D. Hart, Plainville; John Rice, Lincoln, both of Mass.

[73] Assignee: Innovasive Devices, Inc., Marlborough, Mass.

[21] Appl. No.: 781,181

[22] Filed: Jan. 9, 1997

Related U.S. Application Data

[63] Continuation of Ser. No. 643,267, May 3, 1996, which is a continuation of Ser. No. 314,244, Sep. 28, 1994, abandoned.

[51] Int. Cl.$^6$ .................................................. A61B 17/04
[52] U.S. Cl. ............................ 606/148; 606/139; 606/144
[58] Field of Search ............................... 606/148, 139, 606/232, 233, 205, 206, 207, 144, 147

[56] References Cited

U.S. PATENT DOCUMENTS

| | | |
|---|---|---|
| 2,199,025 | 4/1940 | Conn. |
| 3,541,591 | 11/1970 | Hoegerman. |
| 3,625,220 | 12/1971 | Engelsher. |
| 3,766,610 | 10/1973 | Thorsbakken. |
| 3,845,772 | 11/1974 | Smith. |
| 3,934,592 | 1/1976 | Wolvek et al.. |
| 3,959,960 | 6/1976 | Santos. |
| 3,976,079 | 8/1976 | Samuels et al.. |
| 4,275,736 | 6/1981 | Chodorow et al.. |
| 4,408,938 | 10/1983 | Maguire. |
| 4,773,421 | 9/1988 | Davis. |
| 4,871,289 | 10/1989 | Choiniere. |
| 4,890,615 | 1/1990 | Caspari et al.. |
| 4,938,760 | 7/1990 | Burton et al.. |
| 4,957,498 | 9/1990 | Caspari et al.. |
| 5,013,292 | 5/1991 | Lemay. |
| 5,078,731 | 1/1992 | Hayhurst. |
| 5,100,418 | 3/1992 | Yoon et al.. |
| 5,116,337 | 5/1992 | Johnson. |
| 5,133,724 | 7/1992 | Wilson, Jr. et al.. |
| 5,149,329 | 9/1992 | Richardson. |
| 5,152,763 | 10/1992 | Johnson. |
| 5,192,287 | 3/1993 | Fournier et al.. |
| 5,193,933 | 3/1993 | Mailey. |
| 5,211,650 | 5/1993 | Noda. |
| 5,219,359 | 6/1993 | McQuilkin et al.. |
| 5,224,946 | 7/1993 | Hayhurst et al.. |
| 5,236,445 | 8/1993 | Hayhurst et al.. |
| 5,250,053 | 10/1993 | Snyder. |
| 5,268,001 | 12/1993 | Nicholson et al.. |
| 5,279,311 | 1/1994 | Snyder. |
| 5,282,832 | 2/1994 | Toso et al.. |
| 5,306,290 | 4/1994 | Martins et al.. |
| 5,318,579 | 6/1994 | Chow. |
| 5,354,298 | 10/1994 | Lee et al.. |
| 5,372,604 | 12/1994 | Trott. |
| 5,382,258 | 1/1995 | Chow. |

(List continued on next page.)

FOREIGN PATENT DOCUMENTS

| | | |
|---|---|---|
| 1005306 | 2/1977 | Canada. |
| 0 280 572 A1 | 8/1988 | European Pat. Off.. |
| 0 361 756 A1 | 4/1990 | European Pat. Off.. |
| 2.178.908 | 11/1973 | France. |
| 2 628 964 | 9/1989 | France. |
| 2 682 867 | 4/1993 | France. |
| 1 958 429 | 7/1971 | Germany. |
| WO 91/16854 | 11/1991 | WIPO. |
| WO 93/19678 | 10/1993 | WIPO. |

*Primary Examiner*—Michael Buiz
*Assistant Examiner*—Kevin Truong
*Attorney, Agent, or Firm*—Choate, Hall & Stewart

[57] ABSTRACT

A suture tensioning device is described that comprises first and second jaws in facing relationship and oriented in parallel to each other. The first and second jaws are disposed in relative slidable engagement so that one of the jaws is adapted for parallel movement towards and away from the other jaw to define a variable gap between them. A suture retainer is engaged with a surface of the second jaw to enable a suture to be tied so that the suture exerts a variable tension on the surface caused by the variable gap between the first and second parallel jaws. Preferably, the first jaw has defined therein a shape designed to engage with a surface from which a suture emanates. Methods for adjustably tensioning a suture and a kit for performing suspension of a tissue are described.

20 Claims, 2 Drawing Sheets

U.S. PATENT DOCUMENTS

| | | |
|---|---|---|
| 5,417,712 | 5/1995 | Whittaker et al. . |
| 5,425,737 | 6/1995 | Burbank et al. .................. 606/139 |
| 5,458,601 | 10/1995 | Young, Jr. et al. . |
| 5,464,427 | 11/1995 | Curtis et al. . |
| 5,472,452 | 12/1995 | Trott . |
| 5,480,403 | 1/1996 | Lee et al. . |
| 5,486,197 | 1/1996 | Le et al. . |
| 5,489,210 | 2/1996 | Hanosh . |
| 5,490,856 | 2/1996 | Person et al. ........................... 606/139 |
| 5,496,326 | 3/1996 | Johnson . |
| 5,501,683 | 3/1996 | Trott . |
| 5,501,695 | 3/1996 | Anspach, Jr. et al. . |
| 5,522,845 | 6/1996 | Wenstrom, Jr. . |
| 5,545,180 | 8/1996 | Le et al. . |
| 5,571,104 | 11/1996 | Li . |

SUTURE TENSIONING DEVICE

This is a continuation of copending application(s) Ser. No. 08/643,267 filed on May 3, 1996, now pending, which application is a continuation of U.S. Ser. No. 08/314,244, filed Sep. 28, 1994, now abandoned.

BACKGROUND OF THE INVENTION

Stress incontinence is caused primarily by increased intra-abdominal pressure. One surgical method for treating this condition involves suspension of the bladder neck for repositioning in the correct, fixed retropubic position so that there is no voiding of the bladder under stress. Several relatively non-invasive surgical procedures for bladder neck suspension are described in Hadley et al., *Urologic Clinics of North America*, Vol. 12, No. 2, p. 291 (1985).

In the original Pereyra method (*West. J. Surg.*, 67: 223, 1959), a needle is passed from a suprapubic incision to an incision in the vagina near the bladder neck. Stainless steel suture wire is passed several times from the bladder neck to the suprapubic incision to suspend the bladder neck. The Cobb-Radge method inserts the needle from below through the vaginal incision. The Stamey procedure (*Ann. Surg.*, 192: 465, 1980) uses an endoscope to prevent the surgical needle from puncturing the bladder. Dacron vascular graft is used to anchor nylon suture in the periurethral tissue. Finally, in the Raz method (*Urology*, 17: 82, 1981) the surgeon inserts his or her finger through the vaginal incision to guide the suspension needle and avoid penetration of the bladder by the needle. The sutures are anchored by threading through tissue of the vaginal wall and tissue in the suprapubic area.

A major problem encountered during surgical needle suspension procedures such as described above is the correct positioning of the bladder neck and the urethra such that the position of the bladder neck with respect to the bladder is high enough to avoid incontinence under stress while not too high to prevent proper bladder voiding.

Over the years, various techniques have been developed using pubic bone fixation to suspend sutures. To facilitate the anchoring of the suspending suture to the pubic bone with minimal soft tissue dissection, bone anchors with attached sutures are passed into a hole drilled in the pubic bone. Currently, a surgeon may place the tip of his or her index finger on the pubic bone anchor and tie down the suspending suture over his or her index finger using the approximate dimension of the distal pulp of the index finger to deliver a certain degree of tension to the suspending sutures. Once the finger is withdrawn, this leaves a small mount of slack in the suture which permits a quasi-controlled and limited suspension of the bladder neck when suspended in this way. The slack is generally acceptable because of the large volume of pubocervical fascia lending support to the bladder neck. It is, however, relatively easy to place excessive tension on the bladder neck. Chronic urine retention with endoscopic bladder neck suspension has been reported in as many as 5 to 18.9 percent of patients. Excessive tension with overcorrection of the bladder neck is also known to account for bladder instability.

As an alternative to forming a suture sling by tying down against the index finger, there is a need for a suture tensioner for providing consistent, repeatable mounts of tension in the suture sling. A reproducible technique of tying the suspending suture is not presently available.

SUMMARY OF THE INVENTION

The present invention is a suture tensioning device that comprises first and second jaws in facing relationship and oriented in parallel to each other. One of the jaws is adapted for slidable and parallel movement towards and away from the other jaw to define a variable gap between the two jaws. A support arm is connected to the first and second jaws and a suture retainer is engaged with the second jaw. Preferably, the first jaw has defined therein a shape designed to engage with a surface from which a suture emanates. A suture tied off using the suture retainer exerts a variable tension on the surface caused by the variable gap between the first and second parallel jaws.

A preferred device for variably tensioning a suture includes two L-shaped support elements, each element having a shorter and a longer arm in orthogonal relationship. The longer arms of the respective support elements are slidably engaged with each other and adapted for movement from a first position, wherein the shorter arms are in registration and spaced apart from each other, to a second position, where the shorter arms are in registration and are closer together or farther apart than at the first position, so that a variable gap between the shorter arms is defined. A suture retainer is engaged with one of the shorter arms and adapted for tying off a suture emanating from a surface. A conforming element is engaged with the other arm. The conforming element is adapted to mate with the surface so that the suture can exert a variable tension on the surface and on any tissue suspended from the surface by the suture. The variable tension is caused by the variable gap of the spaced-apart shorter arms.

A method for suspending a tissue from a surface includes the steps of allowing free ends of suture material to emanate from the surface and then providing a suture tensioning device to the surface. The device includes first and second jaws in facing relationship and oriented in parallel to each other. One of the jaws is adapted for slidable and parallel movement towards and away from the other jaw to define a variable gap between the jaws. A first jaw of the device is then contacted with the surface from which a tissue is to be suspended and a free end of suture material is engaged with (i.e., threaded through) the tissue to be suspended. The free ends of suture material are then contacted with the second jaw and are then tied-off to each other using the second jaw. The tying-off distance from the surface and suspended tissue is determined by the variable gap position between the first and second jaws of the device, so that the tissue is suspended from the surface and the variable gap allows a variable tension to be imparted to the suture material that is suspending the tissue.

A kit for performing suspension of a tissue can include, among other components, the suture tensioning device of the invention; a suture passer; a bone anchor, a drill and drill guide. The kit further includes a tray for carrying at least the bone anchor, suture passer and tensioning device of the invention. All components of the kit may be sterilizable. In preferred kits, the bone anchor is pre-sterilized.

The use of the present suture tensioner can minimize post-operative urinary blockage caused by excessive tension, and can minimize post-operative urinary incontinence due to insufficient tension. In addition, the suture tensioner permits the visualization of suture knots during tying, thereby ensuring consistency of alignment of knot loops. The suture tensioner also permits consistent and reproducible tension to be applied to a suture.

BRIEF DESCRIPTION OF THE DRAWINGS

FIG. 2A is a frontal, partial cut-away view of one embodiment of the suture tensioning device;

FIG. 2B is a cross-sectional view of one embodiment of the suture tensioning device;

DETAILED DESCRIPTION OF THE INVENTION

Figure 1:
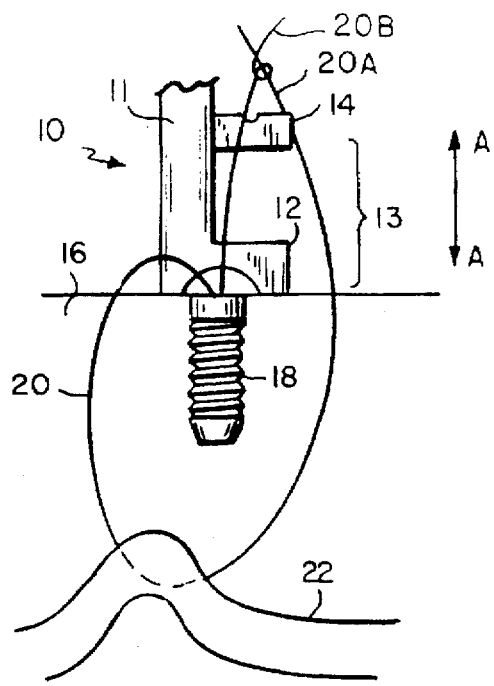
FIG. 1 is a schematic illustration of the suture tensioning device of the present invention deployed in use.

FIG. 1 schematically illustrates a suture tensioning device 10 of the invention in place within the body. The device 10 includes a first jaw 12 and second jaw 14 that are in facing relationship and are preferably in registration so that the jaws 12, 14 are oriented parallel to each other. Jaws 12, 14 are connected to at least one support arm 11. In FIG. 1, each of the jaws 12, 14 are shown slidably engaged to the other by way of a single arm 11. It will be understood that two separate support arms 11 may also be utilized. The first 12 and second jaws 14 can slide relative to each other along the support arm 11 in the direction shown by the double headed arrows A. This may be accomplished by allowing jaw 12 to be fixed and having jaw 14 slide. Conversely, jaw 14 may be fixed and jaw 12 may slide. Whatever slidable engagement is accomplished, the arrangement of the parallel jaws 12, 14 defines a variable gap 13 between them when the jaws move towards and away from each other (hereinafter "to and fro" movement). In the preferred embodiments the respective jaws are parallel to each other. Nevertheless, those having ordinary skill in the art will readily appreciate that the either one or both of the jaws may be hinged to allow for non-parallel orientation.

In FIG. 1, jaw 12 is disposed against a hard tissue 16 (i.e., a bone) into which has been emplaced in bone anchor 18. The bone anchor may be of any conventional design. A preferred bone anchor is described in U.S. Pat. No. 5,268,001 (Nicholson et at.), incorporated herein by reference. A particularly preferred bone anchor is that described in FIGS. 5 and 10 of co-pending and commonly assigned U.S. patent application No. 08/163,130, "Bone Fastener", filed Dec. 6, 1993, incorporated herein by reference. Briefly, this bone anchor is provided with a channel to receive an intermediate portion of a suture (i.e., a segment between the free ends) to form a so-called "slidable" suture element.

Referring again to FIG. 1, with a slidable bone anchor, a single suture 20 is threaded onto the bone anchor 18. Alternately, a pair of separate sutures may emanate from bone anchor 18. A first free end 20A of the suture is threaded through tissue 22 to be suspended and then the free end 20A is engaged with the second jaw 14 of the device. The other free end 20B of the suture that emanates from bone anchor 18 is engaged with second jaw 14 and knotted or otherwise affixed to the first free end 20A. It will be appreciated that the variable gap 13 defined by the distance between jaws 12, 14 will allow a surgeon to modify the tension of the sutures 20 to suit the particular tissue(s) that are to be suspended. The distance that the tissue is suspended may vary although in the case of operations for stress urinary incontinence, the suspension distance (i.e., the gap 13) ) may be several inches. Tissue 16 does not necessarily have to be a bone (e.g., a pubic bone) but may also be soft tissue. Tissue 22 to be suspended may include the bladder neck or may just as conveniently be another tissue, for example the anterior cruciate ligament of the knee. When the present device 10 takes the place of the distal end of the index finger, it allows reproducible tying of the suspending sutures, as described in more detail below.

Figure 2A:
FIG. 2A–2B illustrates one embodiment of the suture tensioning device.
Figure 2B:
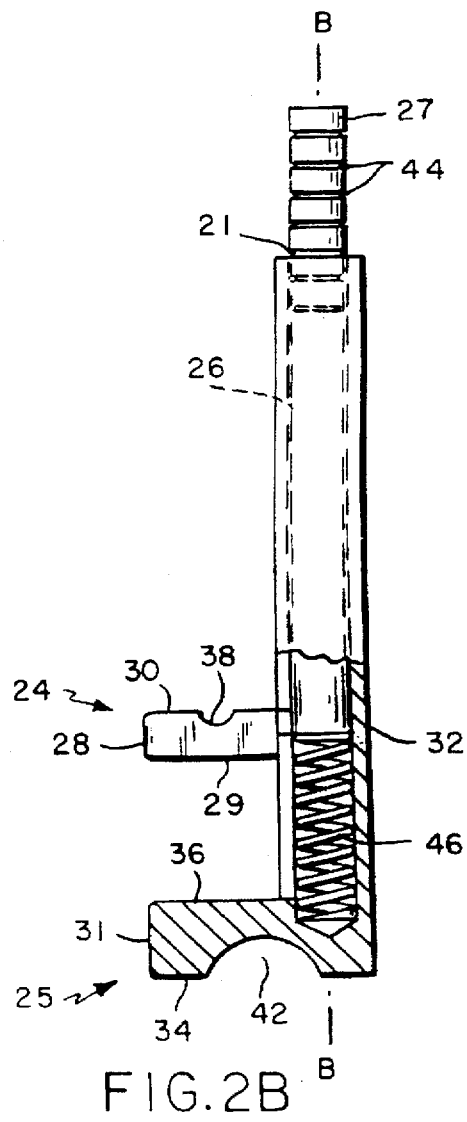

A preferred embodiment of the invention is illustrated in FIGS. 2A and 2B. The device includes a pair of L-shaped support elements 24, 25. A first support element 24 includes a first support arm 26 integral with, and in orthogonal relationship to, a shorter first contact arm 28. Contact arm 28 includes a distal face 29 and a proximal face 30. The term "distal" refers to that portion of the contact arm 28 closest to the tissue to be suspended or from which sutures emanate. Similarly, the second support element 25 also includes a shorter, second contact arm 31 integral with, and in orthogonal relationship to, a longer support arm 32. The second contact arm 31 also has distal 34 and proximal 36 faces.

A suture retainer 38 is disposed upon the proximal face 30 of the first contact arm 28. Suture retainer 38 may include any number of suture retaining configurations, such as a slit in the proximal face 30, a groove in the proximal face 30, a clip or wire engaged with the proximal face 30, and the like. The purpose of the suture retainer 38 is to hold the sutures in place for convenient tying. In the most preferred embodiment, suture retainer 38 is a groove defined in the proximal face 30 of the first contact arm 28.

Engaged with the second contact arm 31, most preferably on the distal face 34 thereof, is a conforming element 42 that is adapted to mate with a peripheral surface of the tissue or bone from which the sutures emanate. The conforming element 42 may include an elastomer disposed on distal face 34 that conforms to the shape of the tissue or bone to which it is mated. More preferably, however, the conforming element 42 is a shape defined in the distal face 34 that is designed to substantially conform to the shape of the tissue/bone interface that is to be contacted with the second contact arm 31. For example, if the device is used to suspend the bladder neck from the pubic bone, which has a slightly curved surface, the distal face 34 on the second contact arm 31 will be designed and to have a slightly arcuate form in order to allow the second contact arm 31 to engage and attain some purchase on the pubic bone.

The respective support arms 26, 32 in FIGS. 2A and 2B are preferably in telescoping relationship so that the outer diameter of support arm 26 is smaller than the inner diameter of support arm 32. Preferably, the second support arm 32 is hollow with a channel 23 defined in it into which the first support arm 26 is disposed in slidable engagement. A bias element 46, such as a spring or elastomeric material, is disposed in channel 23 within support arm 32 between the first 28 and second 31 contact arms and is in simultaneous contact with each contact arm. Element 46 provides some resistance to the to and fro movement of the parallel, registered contact arms 28, 31.

In the most preferred embodiments, bias element 46 is calibrated so that when the two contact arms 28, 31 are moved towards each other, it is possible to know how much force is required. As a further aid in determining the correct suture tension, a series of calibration marks 44 may be formed on the outer peripheral surface 27 of support arm 26. When no bias pressure is applied to the contact arms, a portion of support arm 26 extends out of the proximal end 21 of support arm 32. The calibration marks 44 on that portion of arm 26 will be visible to the surgeon as an aid to correctly judge the exact tension on the suture. As biasing pressure is applied to force the contact arms together, the calibration marks will be increasingly not visible as the support arm 26 enters support arm 32. These marks and the bias element, in combination with the movable contact arms 28, 31, allows a surgeon to select a particular tension on the sutures without having to rely on guesswork. In addition to providing a reproducible amount of tension in the tied suture, the use of the present device 10 spaces the knot of the suture apart from the tissue during tying and allows visualization of the knot while it is being tied.

Figure 3:
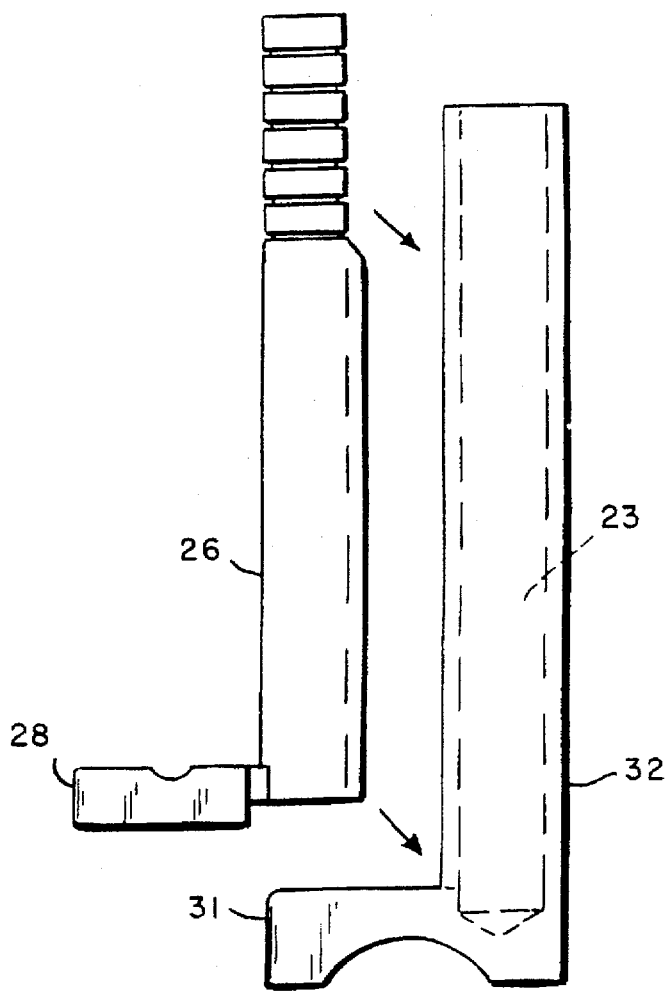
FIG. 3 is an exploded view of another embodiment of the suture tensioning device.

In another embodiment, to and fro movement of the parallel contact arms may also be accomplished by providing second support arm 32 with a channel 23 defined in a peripheral surface thereof and by providing first support arm 26 with a dovetail 27 (see FIG. 3) or other similar arrangement to mate with channel 23 which will also allow for slidable engagement of the support elements. Other configurations for allowing the to and fro movement of the support elements, and thus to and fro movement of the parallel, registered contact arms, are readily ascertained by those of ordinary skill in the art.

Figure 4:
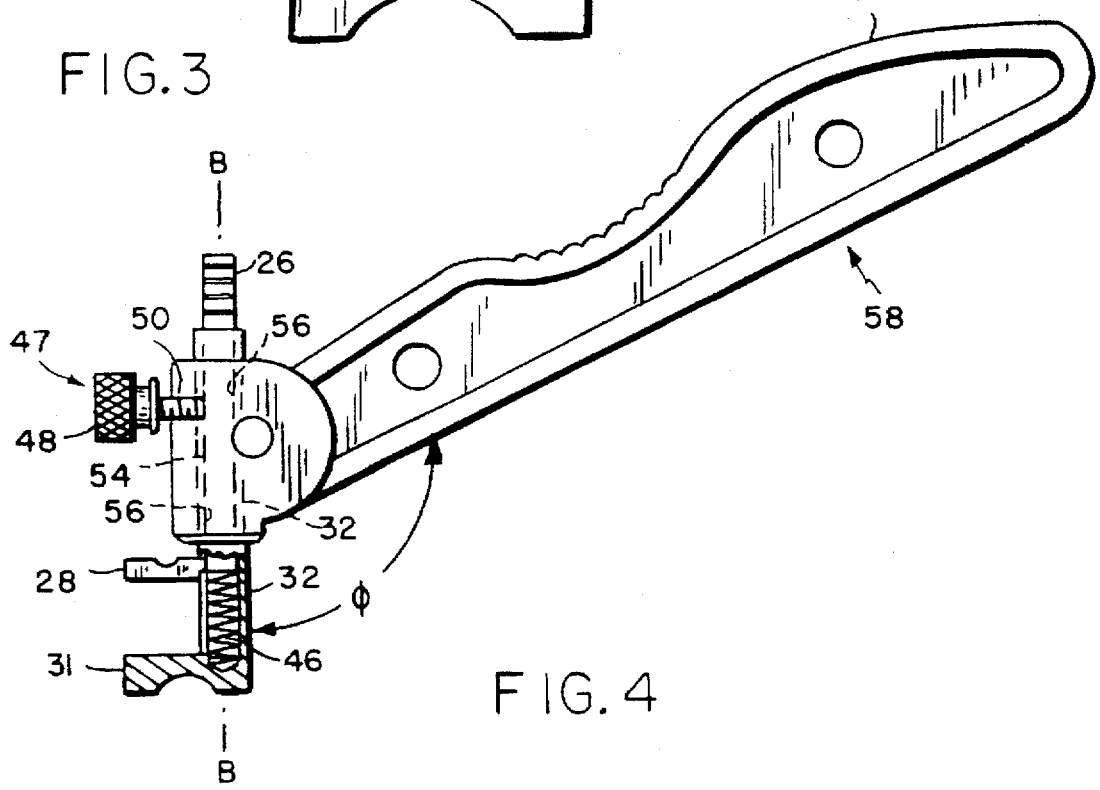
FIG. 4 is a plan view of a second embodiment of the suture tensioning device of the invention, with the support elements shown in cut-away cross-section.

In most preferred embodiments of the invention, as illustrated in FIG. 4, a handle 58 is engaged with second support arm 32. The handle 58 consists of a manually graspable gripping element 59 integral with a tubular head 60. The second support arm 32 is engaged with handle 58 via the head 60, or alternatively, by integral molding of the grasping element 59, head 60 and second support arm 32 during manufacture. The second support arm 32 may thus be fixed to the handle 58 and the angle (φ) subtended by the long axis B—B of support arms 26, 32 and element 59 is generally about 90 degrees. Nevertheless, it will be understood that the attachment of the handle 58 to the support arms 32 may be a made using a pivoting attachment so that the angle subtended by the support elements and handle may vary considerably within a wide range depending on the circumstances of the surgery.

Illustrated in FIG. 4 is a stop 47 which is used to prevent further to and fro movement of the parallel contact arms once the appropriate suture tension (i.e. gap width) is reached. In FIG. 4, the stop 47 consists of a nut 48 connected to a threaded rod 50 that is engaged into an aperture (not shown) in the outer peripheral surface 54 of second support arm 32. The rod 50 then frictionally engages with an outer peripheral surface 56 of the first support arm 26, preventing the first support arm 26 from further telescoping movement within the second support arm 32. It will be appreciated that other mechanisms may employed to lock the first and second support arms to each other. For example, a ratchet, cam or other means that allows for releasable frictional engagement of the first and second support arms may be used. The exact mechanism is not intended to limit the invention in any way.

The suture tensioning device 10, in particular the L-shaped support elements, is preferably made of materials that are biocompatible. The term "biocompatible" means that the material is chemically and biologically inert. Suitable materials must be rigid and include, for example, stainless steel and P1700 polysulfone (Amoco Corporation). The handle 58, may also be made of these materials.

The sutures employed with the device are most preferably not bioabsorbable since the procedures most conveniently used with the present device are designed for long-term tissue suspension. The term "bioabsorbable" refers to those materials that are meant to be decomposed or degraded by bodily fluids, such as, for example, blood and lymph. Exemplary sutures include Number 2 non-bioabsorbable, monofilament sutures (manufactured, for instance, by Davis and Geck, Co., Danbury, Conn.; manufactured under the tradename "Prolene" by Ethicon, Corp. N.J.). If, however, circumstances permit use of bioabsorbable sutures, known bioabsorbable polymers and copolymers range in degradation time from about 3 months for polyglycolide to about 48 months for polyglutamic-co-leucine. A common bioabsorbable polymer used in absorbable sutures is poly (L-lactide) which has a degradation time of about 12 to 18 months. Other polymers are derived from glycolic and lactic acids, such as a synthetic polyester chemically similar to other commercially available glycolide and lactide copolymers. Glycolide and lactide degrade and absorb in the body by hydrolysis into lactic acid and glycolic acid which are then metabolized by the body.

The suture tensioning device of the invention may be fabricated using a variety of conventional methods. For example, a tensioning device made of a biocompatible plastic is made by injection molding. Machining procedures are suitable for stainless steel devices.

There is no limit to the size of the device and the dimensions of the device will vary depending upon the surgical procedure and size of the sutures. Exemplary dimensions of a typical device of FIG. 4 include a handle about 4.5" (114 mm) long. Arm 32 is about 1.5" (38 mm) long and arm 26 is about 1.25" (31 mm) long. The contact arms are each about 0.25" (6.3 mm) long. Threaded rod 50 is about ⅛" (3 mm) in. length.

The invention also encompasses kits to be used by surgeons. Kits are typically sold in supporting and packaging trays and all components of the kit, including the tray itself, are sterilizable using either autoclave or chemical sterilants such as, for example, ethylene oxide. Exemplary components of a preferred kit are made by Innovasive Devices® Inc., Hopkinton, Mass. 01748 and may comprise the suture tensioning device of the present invention, a speculum, a snare to pass the suture through the tissues (also called a "suture passer"), a bone anchor (See U.S. Pat. No. 5,268, 001), a drill and a drill guide.

The suture tensioning device of the present invention may be used in any surgical operation in which tissues are designed to be suspended, one from the other or are designed to be suspended from bone. As discussed above, the most common use for the present device is in operations to correct stress urinary incontinence. Nevertheless, the device may be also used in orthopedic surgical techniques, such as for example repair of the anterior cruciate ligament. Although many methods have been developed to surgically correct stress urinary incontinence, the following general description of the use of the present device in such an operation is merely exemplary and is not intended to limit the scope of the invention in any way.

Two separated, one inch transverse incisions are made over the pubic bone and dissection is carded down to the area of the rectus fascia. Beginning on the right side, the wound is stretched cephalad to allow the vertical passage of a Stamey needle (Pilling Company, Fort Washington, Pa.) through the rectus fascia. The needle is then sharply angled onto the abdomen so that the point rests on the underside of the pubic periosteum.

The point of the needle, while maintaining contact with the underside of the pubis, is thereafter passed distally toward the introitus. At the completion of this distal passage, the needle can be palpated through the introitus to the right of the urethra. Palpation through the vagina is avoided during this distal passage of the needle to avoid pushing the bladder or urethra into the path of the needle. The tip of the needle is withdrawn from the pubourethral ligament and gently swept along the pubocervical fascia to the area of the bladder neck under the guidance of a finger within the vagina.

The needle is then passed through the pubocervical fascia and vaginal mucosa. A number 1 polypropylene suture is passed through the needle hole and withdrawn with the needle through the pubic wound. The needle is then reintroduced through the rectus fascia 2 cm lateral to the initial passage and through the vaginal mucosa using the same needle passage technique described above. The tip of the needle with the vaginal end of the suture is then withdrawn into the retropubic space and then advanced to a point where it is passed through the vaginal mucosa and passed distal to the introitus.

The suture is then removed from the needle and the needle tip once again withdrawn to the retropubic space and passed through the vaginal mucosa. The vaginal end of the suture is then passed into the needle and pulled up through the pubic wound using the needle. The identical procedure is performed on the left side. A 3.5 mm Innovasive® Devices, Inc. bone anchor (U.S. Pat. 5,268,001) is then used for pubic bone fixation of the suspensory sutures. Two holes are drilled into the pubic bone approximately 2 cm. lateral to the symphysis. One anchor for each side (2 per patient) is loaded with a medical suture end (which had less vaginal contact than the lateral ends, thereby, potentially reducing the chance of bacterial contamination). Each anchor is placed into its hole and each anchor is disposed in place. See, for example, U.S. Pat. No. 5,268,001, incorporated herein by reference. With the Innovasive® anchors, traction is not needed to assure adequate fixation of the anchors.

The sutures are then tied down with controlled tension so as to develop a gentle elevation and cradle-like support of the bladder neck. The second contact arm of the device is mated with the pubic bone in the vicinity of the bone anchors. The distance between the contact arms may be varied at this point, although it is preferable to adjust the distance between the contact arms prior to the operation. The free end of the sutures on each side of the bladder neck are threaded through the bladder neck and the other free end of the sutures is engaged with the first contact arm of the device. The free ends of the sutures are tied together as in FIG. 1 in a controlled and reproducible manner.

To repair a cruciate ligament, one end of the ligament is fixed into the femur. The other end of the ligament is threaded with sutures and is pulled through a hole in the tibia. The sutures are temporarily tied using the tensioning device of the present invention to tension the ligament so that a range of motion can be performed, as a test for the ligament tension. If the tension needs to be adjusted, the suture knots may be conveniently be tightened or slackened, if needed, using the adjustable arms of the device and the range of motion test performed again. This is repeated until the surgeon is comfortable with the results.

Equivalents

It should be understood that various changes and modifications of the preferred embodiments may be made within the scope of the invention. Thus it is intended that all matter contained in the above description be interpreted in an illustrative and not limited sense.

We claim:

1. A suture tensioning device, comprising:
   a support arm;
   a first jaw attached to said support arm;
   a second jaw slidably attached to said support arm in facing relationship with and oriented in parallel to said first jaw, so that said second jaw is adapted for slidable and parallel movement towards and away from said first jaw, said jaws defining a variable gap therebetween; and
   a suture retainer on said first or second jaw.

2. The device of claim 1, wherein said suture retainer is on said second jaw and said first jaw is shaped to conform to a surface from which a suture emanates.

3. The device of claim 2, wherein said support arm comprises first and second support arms, said first jaw is mounted on said first support arm in an orthogonal relationship, and said second jaw is mounted on said second support arm in an orthogonal relationship.

4. The device of claim 3, wherein said first and second support arms are telescopingly disposed relative to each other to allow said first and second jaws to slide relative to each other.

5. The device of claim 4, wherein said first support arm has a channel defined therein and said second support arm includes a dovetail for slidable engagement with said channel of said first support arm.

6. The device of claim 4, further comprising a biasing element disposed inside said first support arm and engaged with said second support arm.

7. The device of claim 3, further comprising a stopper attached to the device in such a way that it is capable of being engaged with at least one support arm for fixing a position of said first and second jaws relative to each other without slidable movement.

8. The device of claim 7, further comprising a manually graspable handle attached to at least said first support arm.

9. The device of claim 8, wherein said handle is arranged at an angle relative to said first support arm.

10. The device of claim 9, wherein said handle is adjustably mounted on said first support arm so that said angle between said handle and said first support arm may be varied.

11. A kit for performing suspension of a tissue, comprising:
    a suture tensioning device, comprising:
      a support arm;
      a first jaw attached substantially perpendicular to said support arm;
      a second jaw slidably attached and substantially perpendicular to said support arm in facing relationship with and oriented in parallel to said first jaw, so that said second jaw is adapted for slidable and parallel movement towards and away from said first jaw, said jaws defining a variable gap therebetween; and
      a suture retainer on said first or second jaw;
    a suture passer; and
    a bone anchor.

12. The kit of claim 11, further comprising a tray for supporting and packaging said bone anchor, suture passer and suture tensioning device.

13. The kit of claim 12, wherein said suture tensioning device and suture passer are sterilizable.

14. A suture tensioning device comprising:
    a first L-shaped member comprising a first support arm attached substantially perpendicularly to a first jaw, said first support arm being hollow and having a channel therein;
    a second L-shaped member comprising a second support arm attached substantially perpendicularly to a second jaw, said second support arm being disposed in a slidable telescoping arrangement within said channel in said first support arm so that said first and second jaws extend from said telescoped support arms in substantially facing parallel arrangement, and define a variable gap therebetween; and a suture retainer on said second jaw.

15. The device of claim 14, further comprising a bias element disposed within said channel in contact with said second support arm at a point at which said second support arm is attached to said second jaw, said bias element providing some resistance against relative motion of said first and second L-shaped members.

16. The device of claim 15, wherein said bias element is calibrated to indicate how much force is exerted when said L-shaped members are moved relative to each other.

17. A suture tensioning device comprising:
  a first L-shaped member comprising a first support arm attached substantially perpendicularly to a first jaw, said first support arm being having a channel defined in a peripheral surface thereof;
  a second L-shaped member comprising a second support arm attached substantially perpendicularly to a second jaw, said second support arm including a dovetail element, said dovetail element being slidably engaged with said channel in said first support arm so that said first and second jaws extend from said telescoped support arms in substantially facing parallel arrangement, and define a variable gap therebetween; and
  a suture retainer on said second jaw.

18. A kit for performing suspension of a tissue, comprising:
  a device for variably tensioning a suture, comprising:
    first and second L-shaped support elements in sliding engagement with one another, said first L-shaped support element comprising:
      a first short arm; and
      a first long arm attached to said first short arm in an orthogonal relationship, said second L-shaped support element comprising:
      a second short arm; and
      a second long arm attached to said second short arm in an orthogonal relationship, said first and second L-shaped support elements being arranged relative to one another so that said first and second short arms are in registration with one another and define a gap of variable size therebetween, said size of said gap being changeable by motion of one of said L-shaped support elements relative to said other L-shaped support element;
    a conforming element on said first short arm, said conforming element being shaped to matingly engage a surface from which a suture emanates; and
    a suture retainer on said second short arm, said suture retainer adapted for tying off ends of said suture emanating from said surface,
    said device being arranged and constructed so that said tied-off suture exerts a tension of variable magnitude on said surface, said magnitude of said tension being determined by said size of said gap between said short arms;
  a suture passer; and
  a bone anchor.

19. The kit of claim 18, further comprising a tray for supporting and packaging said bone anchor, suture passer and suture tensioning device.

20. The kit of claim 19, wherein the suture tensioning device and suture passer are sterilizable.

* * * * *

UNITED STATES PATENT AND TRADEMARK OFFICE
CERTIFICATE OF CORRECTION

PATENT NO. : 5,690,655

DATED : November 25, 1997

INVENTOR(S) : Rickey D. Hart and John Rice

It is certified that error appears in the above-identified patent and that said Letters Patent is hereby corrected as shown below:

Column 3, line 64: please delete the second use of ")".

Column 7, line 26: please delete "thereby,"; and insert therefor --thereby--.

Signed and Sealed this

Seventh Day of April, 1998

Attest:

BRUCE LEHMAN

*Attesting Officer*       *Commissioner of Patents and Trademarks*